(12) United States Patent
Drummy

(10) Patent No.: US 9,176,080 B2
(45) Date of Patent: Nov. 3, 2015

(54) X-RAY ANALYSIS APPARATUS WITH DETECTOR WINDOW PROTECTION FEATURE

(75) Inventor: Michael Drummy, North Reading, MA (US)

(73) Assignee: Olympus NDT, Inc., Waltham, MA (US)

( * ) Notice: Subject to any disclaimer, the term of this patent is extended or adjusted under 35 U.S.C. 154(b) by 649 days.

(21) Appl. No.: 13/551,232

(22) Filed: Jul. 17, 2012

(65) Prior Publication Data

US 2013/0022166 A1 Jan. 24, 2013

Related U.S. Application Data

(60) Provisional application No. 61/509,252, filed on Jul. 19, 2011.

(51) Int. Cl.
*G01N 23/223* (2006.01)
(52) U.S. Cl.
CPC ........ *G01N 23/223* (2013.01); *G01N 2223/076* (2013.01)
(58) Field of Classification Search
USPC .............................. 378/44, 45, 140, 160, 161
See application file for complete search history.

(56) References Cited

U.S. PATENT DOCUMENTS 7,796,726 B1 * 9/2010 Gendreau et al. ............... 378/46
2008/0192897 A1 8/2008 Piorek et al.

FOREIGN PATENT DOCUMENTS

| EP | 2 096 431 | 9/2009 |
|---|---|---|
| GB | 2 089 499 | 6/1982 |
| JP | 10-221276 | 8/1998 |
| WO | WO 80/01718 | 8/1980 |
| WO | WO 00-37928 | 6/2000 |

OTHER PUBLICATIONS

Search Report issued on Jun. 18, 2013 by European Patent Office in connection with corresponding European application No. EP 12 17 7028.
Unknown: "Shutters"—Early Photography, Oct. 6, 2010, pp. 1-6, XP002697526; retrieved from Internet: http://web.archive.org/web/20101006054045; http://www.earlyphotography.co.uk/site/shutter.html.

* cited by examiner

*Primary Examiner* — Kiet T Nguyen
(74) *Attorney, Agent, or Firm* — Ostrolenk Faber LLP

(57) ABSTRACT

An X-ray fluorescence (XRF) instrument comprises a handheld device housing which holds a radiation emitter configured to emit radiation directed at a test object and a radiation detector housed inside a chamber closed by a sealing window and configured to detect radiation of the test object, caused by the test object being exposed to the emitted radiation. A protective cover mechanism is affixed to the testing device and is configured to have a closed position which covers or blocks access to the sealing window to protect it from being broken or damaged by debris or other obstructions, and an open position which exposes the sealing window to allow the un-obstructed passage of radiation therethrough. The cover mechanism can be implemented variously, including by a pivotally mounted cover plate, an iris mechanism, a fan-like cover and the like. Debris can be detected variously, including by strain sensors, optical detectors and proximity sensors.

22 Claims, 12 Drawing Sheets

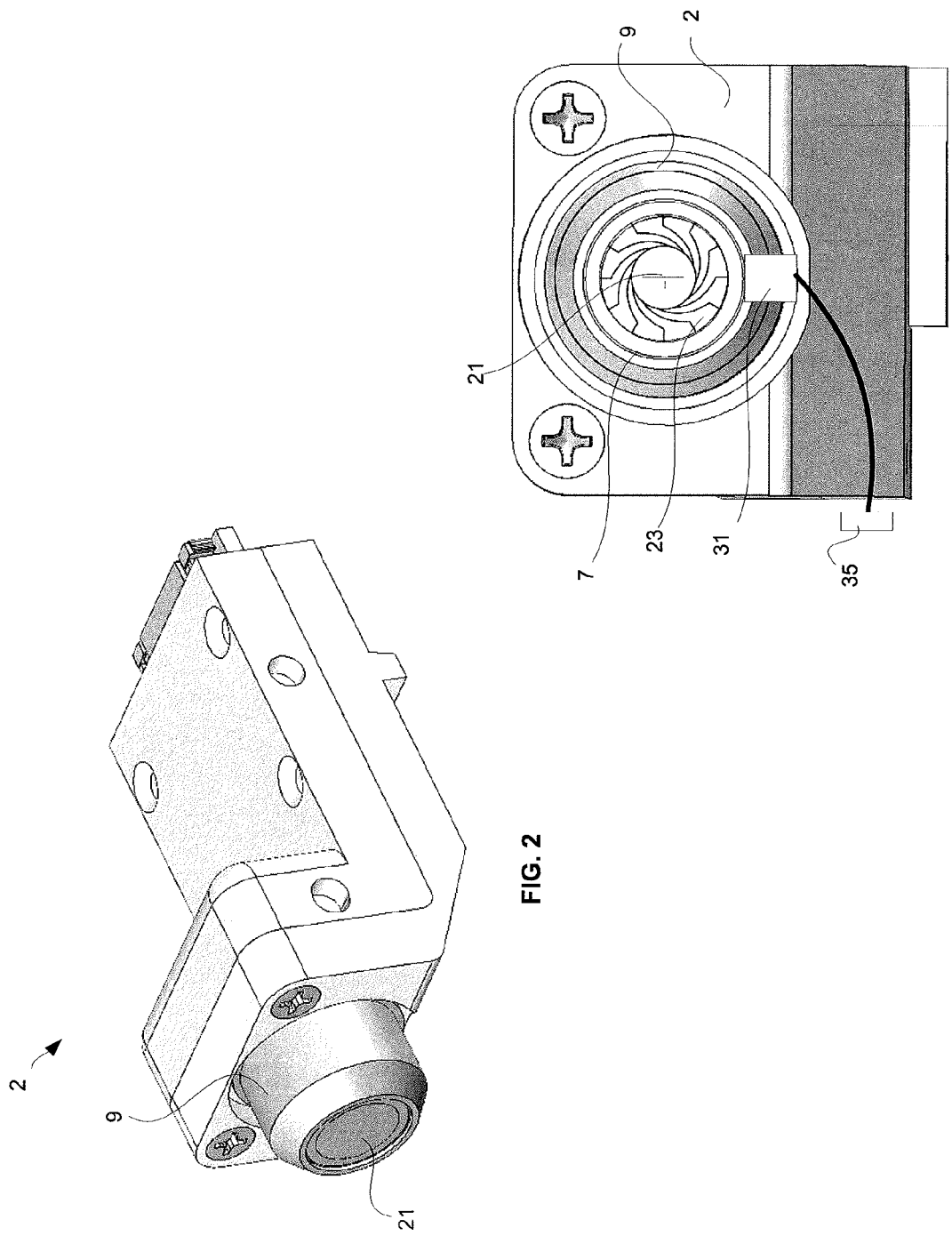

X-RAY ANALYSIS APPARATUS WITH DETECTOR WINDOW PROTECTION FEATURE

CROSS REFERENCE TO RELATED APPLICATION

This application claims the benefit and priority of U.S. Provisional patent application Ser. No. 61/509,252 filed Jul. 19, 2011 entitled X RAY ANALYSIS APPARATUS WITH DETECTOR WINDOW PROTECTION FEATURE, the entire disclosure of which is incorporated herein by reference.

FIELD OF THE INVENTION

The subject invention generally relates to X-ray instruments and, more particularly, to a protection device therefor.

BACKGROUND OF THE INVENTION

X-ray devices such as handheld X-ray fluorescence (XRF) instruments are known as are various shields for such instruments. See U.S. Pat. Nos. 7,430,274; 7,375,359; 7,375,358; 6,965,118; and 7,671,350 as well as WO 00/37928 all incorporated herein by this reference. See also U.S. Published Application No. US-2008-0152079.

In recent years higher performance handheld XRF instruments have started to use larger active area silicon drift detectors (SDD's) in the range of 20 mm$^2$ and greater. These larger area detectors are well suited for measuring low atomic number elements in the field due to their greater sensitivity; however, a drawback of using larger area SDD's is that the sealing windows required to maintain an evacuated chamber in the region of the silicon detector surface become more fragile with increased size. This drawback is exacerbated when a handheld XRF instrument is used in the field environment.

For example, when a handheld XRF instrument is used in mining or scrap metal applications, the measurement head must be placed in close proximity to test substances that may contain various types of debris that can pierce, or otherwise damage, the environmental sealing film and detector sealing window of the instrument. When this occurs, the sealing film can be replaced by the operator; however, the unit must be returned to the factory to have its detector replaced at considerable inconvenience and expense to the owner of the handheld XRF instrument. Accordingly, a solution that protects the detector sealing window while not deteriorating the performance of the handheld XRF instrument would be of great value to the users of these instruments.

SUMMARY OF THE INVENTION

The fragile sealing window used in an X-ray detector can be protected from encounters with foreign objects by applying the embodiments of the present disclosure.

It is the general object of the present disclosure to overcome the problems associated with the background art by introducing an economical, small, and compact instrument that contains a detector window protection system that engages whenever: a) a measurement mode is not active, or b) a penetrating object is sensed to be in close proximity to the detector sealing window during a measurement mode.

The foregoing and other objects of the present disclosure may be realized with a radiation emitting, material testing device which includes a hand held device housing with a radiation emitter therein and configured to emit radiation directed at a test object. A radiation detector is housed inside a chamber closed by a sealing window, which detector is configured to detect radiation emitted from the test object to detect a property of the test object. A protective cover mechanism is affixed to the testing device and is configured to have a closed position which covers or blocks access to the sealing window of the radiation detector and an open position which exposes the sealing window to allow the un-obstructed passage of radiation therethrough.

In accordance with various embodiments of the invention, the protective cover mechanism may comprise a pivotally mounted cover plate which is pivotable between closed and open positions, or an iris mechanism or a fan-like cover with a plurality of plates which can be positioned to overlap one another to expose the sealing window or to spread apart to cover the sealing window. Electromechanical and mechanical devices that drive the pivot motion are also disclosed.

In accordance with preferred embodiments, debris or other obstructions which become positioned close to or which approach the sealing window can be automatically detected to trigger the protective cover mechanism to close. The presence detector can be realized in various ways, including by means of one or more strain sensors, optical detectors and/or proximity sensors, or even combinations thereof.

Other features and advantages of the present invention will become apparent from the following description of the invention which refers to the accompanying drawings.

BRIEF DESCRIPTION OF THE DRAWINGS

FIG. 2 is a schematic diagram showing a detector used in an XRF instrument and its corresponding unprotected sealing window.

FIG. 3 is a schematic side diagram showing a detector used in an XRF instrument, its corresponding sealing window with an iris style deployable protective cover.

Figure 1:
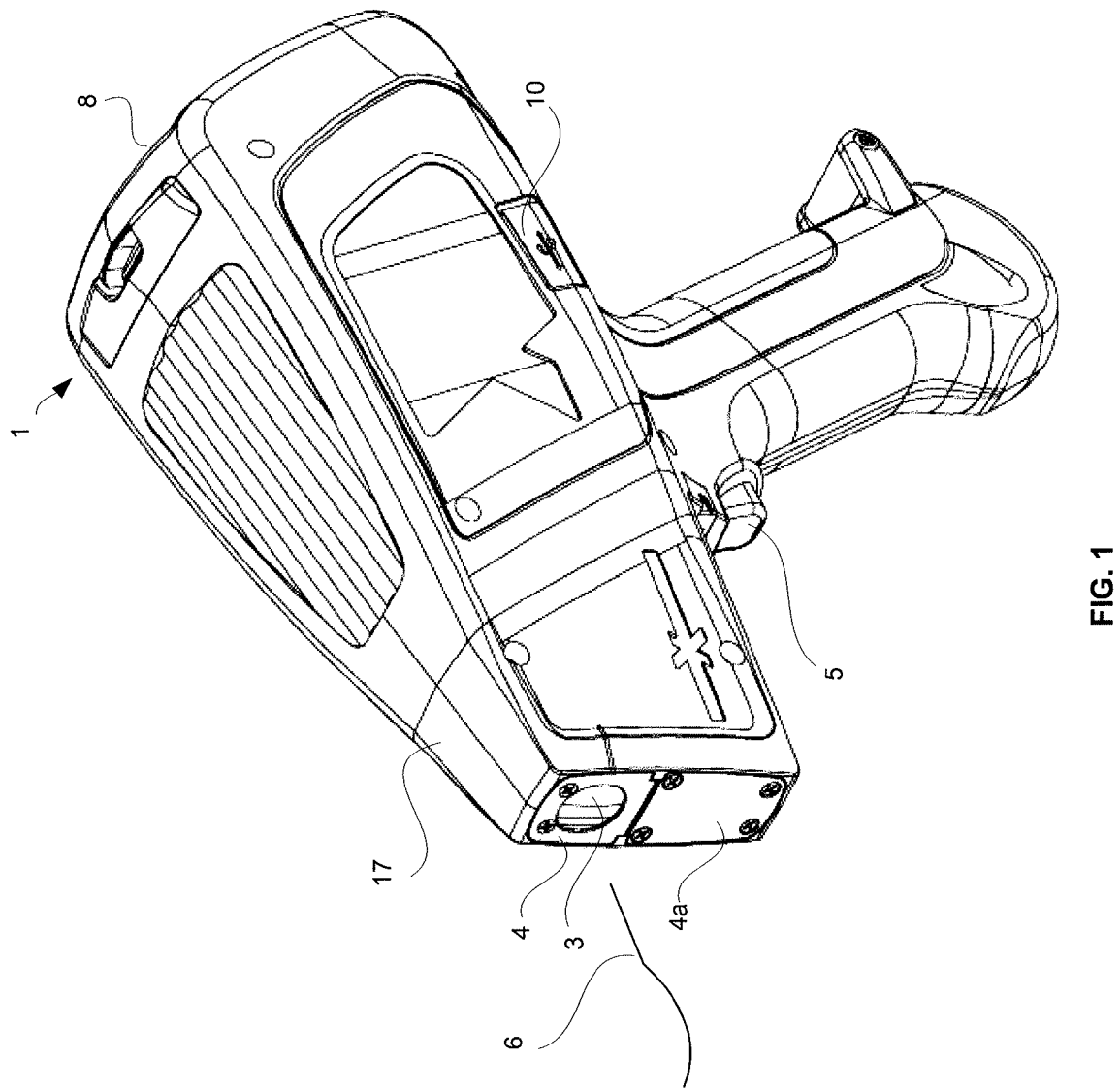
FIG. 1 is a schematic diagram showing the primary components associated with a handheld XRF instrument.

Other features and advantages of the present invention will become apparent from the following description of the invention which refers to the accompanying drawings.

DETAILED DESCRIPTION OF PREFERRED EMBODIMENTS OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. Moreover, the claims hereof are not to be read restrictively unless there is clear and convincing evidence manifesting a certain exclusion, restriction, or disclaimer.

The term "measurement mode" as used in the present disclosure denotes the state of operation of X-ray detector 2 when an XRF measurement is being made. More specifically, a measurement mode is controlled by microprocessor system 51 shown in FIG. 6 and is comprised of: a) exciting sample 121 by X-ray tube 15 to emit its own characteristic X-rays; b) sensing the X-rays emitted from sample 121 by detector 2; and c) processing the output of detector 2 by digitizer 56 and DSP 57 to obtain the desired XRF information.

Elements of Embodiments

FIG. 1 shows an example of an X-ray analysis apparatus, in this particular example, a handheld XRF instrument 1 including measurement head 17, trigger switch 5, display 8, and TO port 10. Affixed to measurement head 17 is support frame 4 for the mounting of sealing film 3. The interior view of measurement head 17 shown in FIG. 4 contains, among other things, X-ray detector 2, window protector 7 with actuator 71, presence sensor 70, detector front housing 9, and X-ray tube 15.

Referring to FIG. 2, sealing window 21 is attached to the front face of detector 2 to create an evacuated chamber between sealing window 21 and the front surface of the silicon detector semiconductor (not shown) located inside of detector 2 for the purpose of allowing adequate detector cooling by a peltier device (not shown). Sealing window 21 is typically made out of a very thin and fragile material, such as 8 μm thick Beryllium (Be). Consequently, sealing window 21 can be easily punctured, or otherwise damaged, when the X-ray analysis apparatus is used in a harsh field environment.

Figure 4:
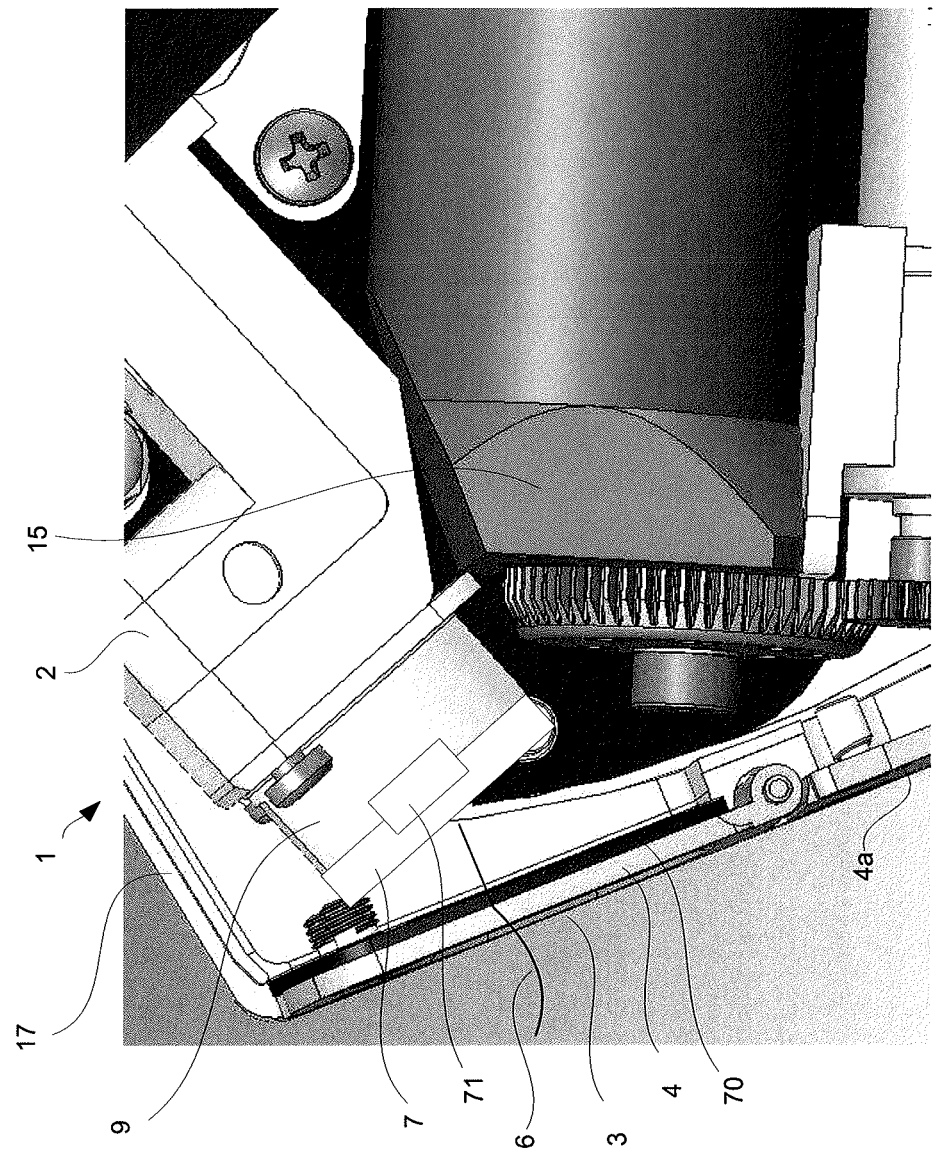
FIG. 4 is another schematic side diagram showing the location and arrangement of a deployable protective cover inside of an XRF instrument.

For example, when handheld XRF instrument 1 (FIG. 1) is used in mining or scrap metal applications, measurement head 17 must be placed in close proximity to test substances that may contain debris 6 which can pierce sealing film 3 and move into the region near sealing window 21 (FIG. 2) and then pierce it. This region is depicted in FIG. 4 between sealing film 3 and detector front housing 9. When this occurs, sealing film 3 can be easily replaced by the operator; however, the unit must be returned to the factory to have detector 2 replaced causing considerable inconvenience and expense to the owner of the XRF instrument.

An arrangement of key elements of the detector window protection system contained within measurement head 17 is shown in FIG. 4 wherein window protector 7 and its associated actuator 71 are attached to detector front housing 9, and presence sensor 70 is attached to support frame 4.

Figure 6:
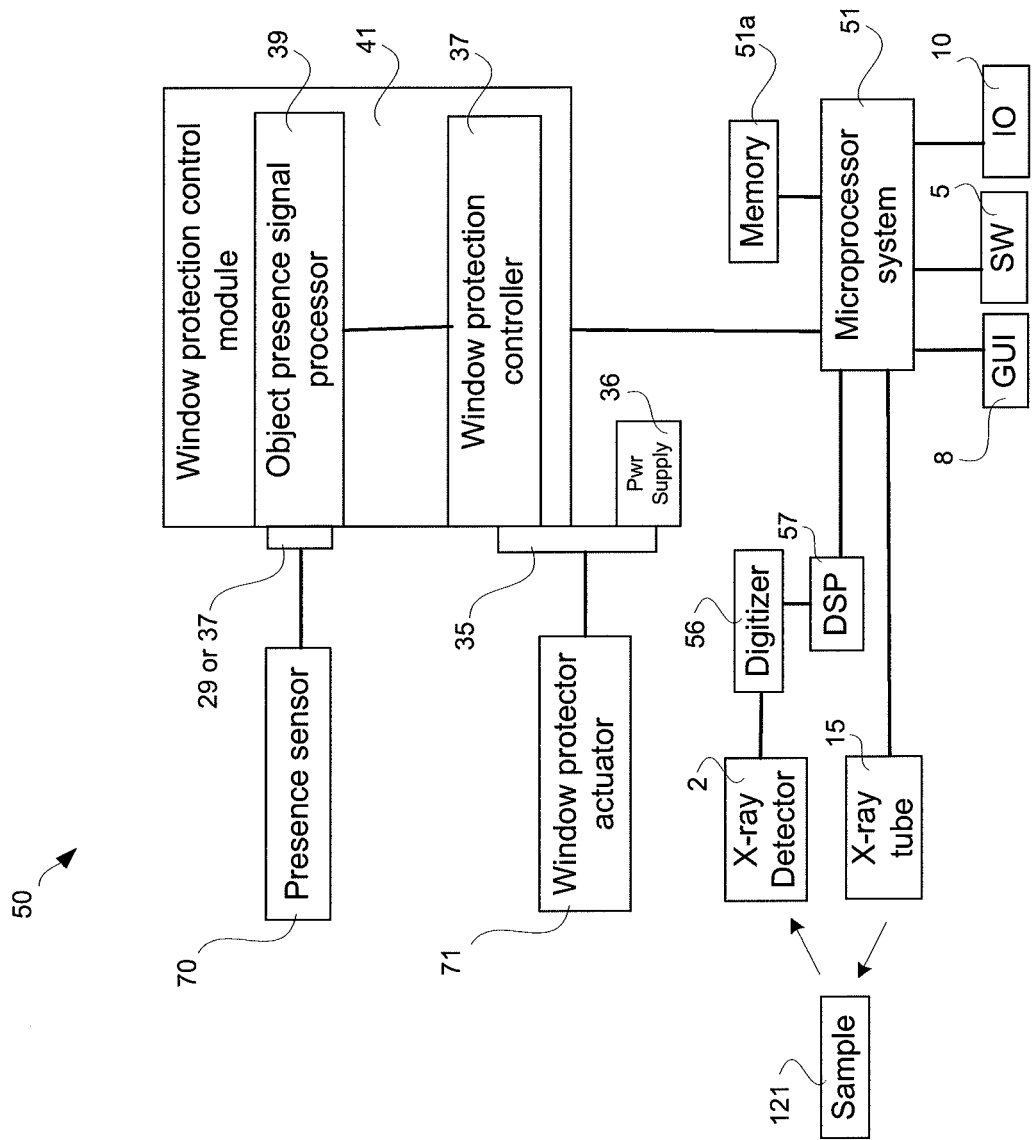
FIG. 6 is a schematic diagram showing the primary components associated with the control system of an XRF instrument.

Control system 50 of XRF instrument 1 shown in FIG. 6 comprises microprocessor system 51, memory 51a, GUI 8, trigger switch 5, input/output connection 10, digital signal processor 57, digitizer 56, X-ray detector 2, X-ray tube 15, presence sensor 70 with cable 29, window protector actuator 71 with cable 35, power supply 36, and window protection control module 41 that includes object presence signal processor 39 and window protection controller 37. Test sample 121 is also shown in FIG. 6.

Figure 8:
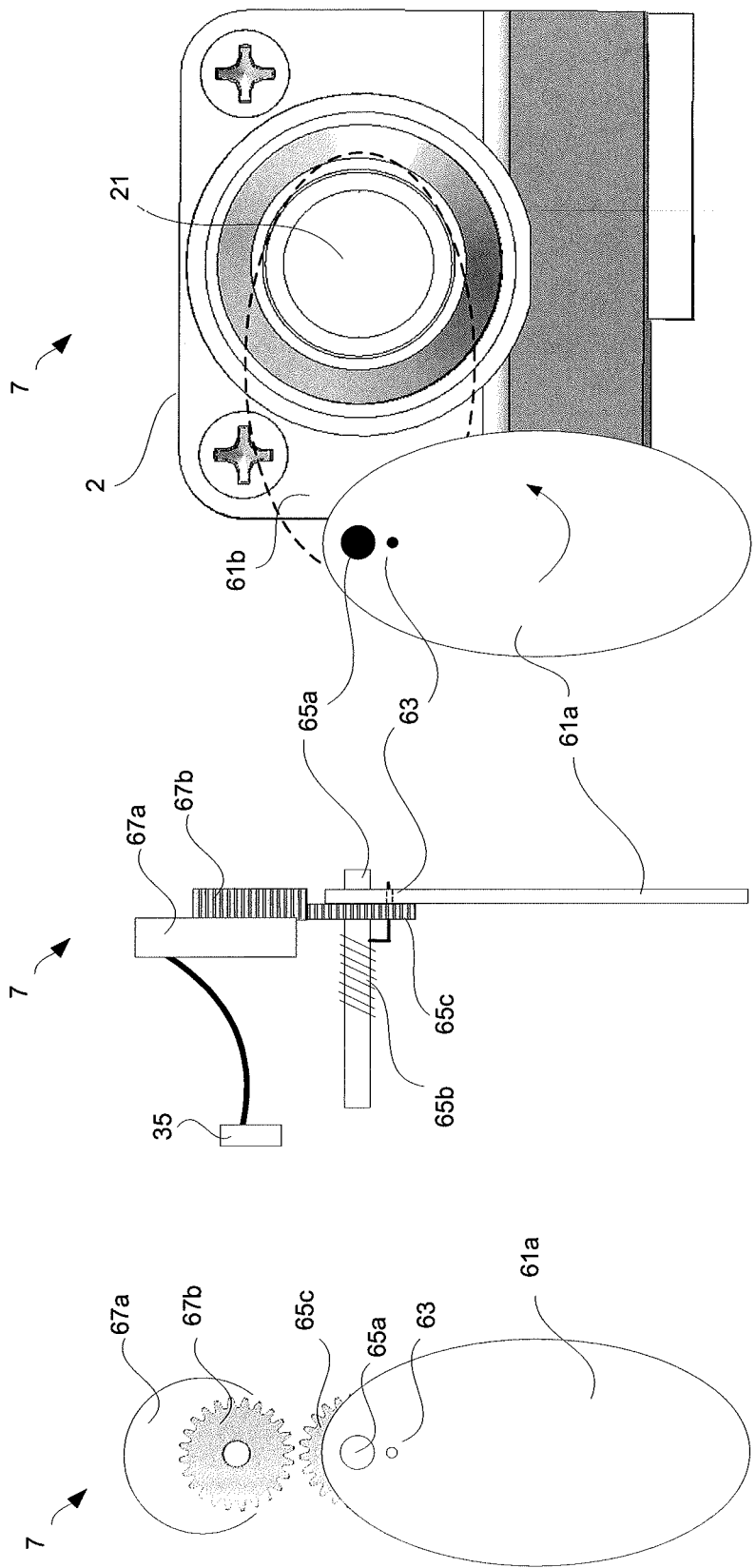
FIGS. 8a, 8b and 8c are schematic diagrams showing the front and partial side views, respectively, of the sealing window protection control system of an XRF instrument.
Figure 11A:
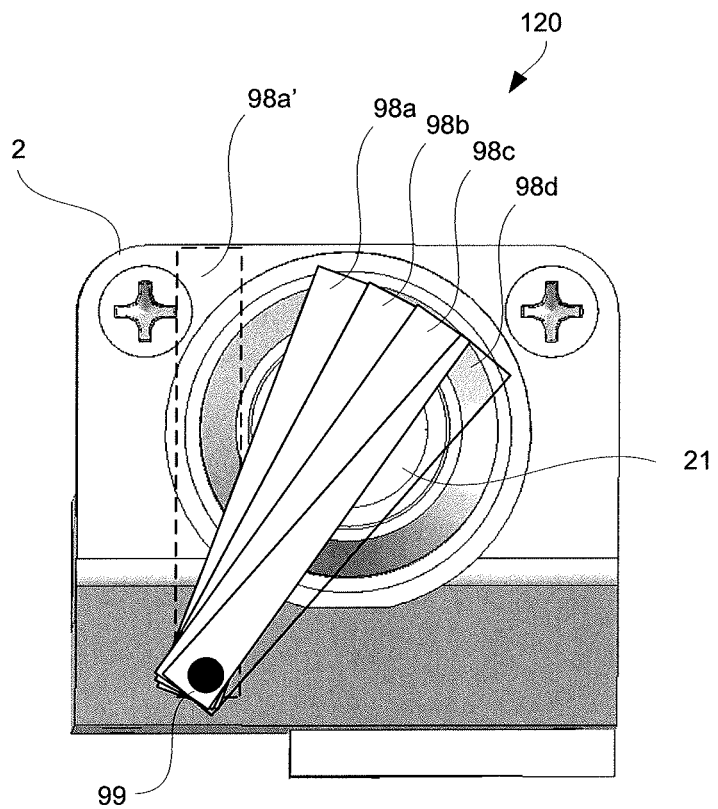
FIG. 11a is a schematic diagram showing the collapsible protective cover embodiment used in an XRF instrument.
Figure 11B:
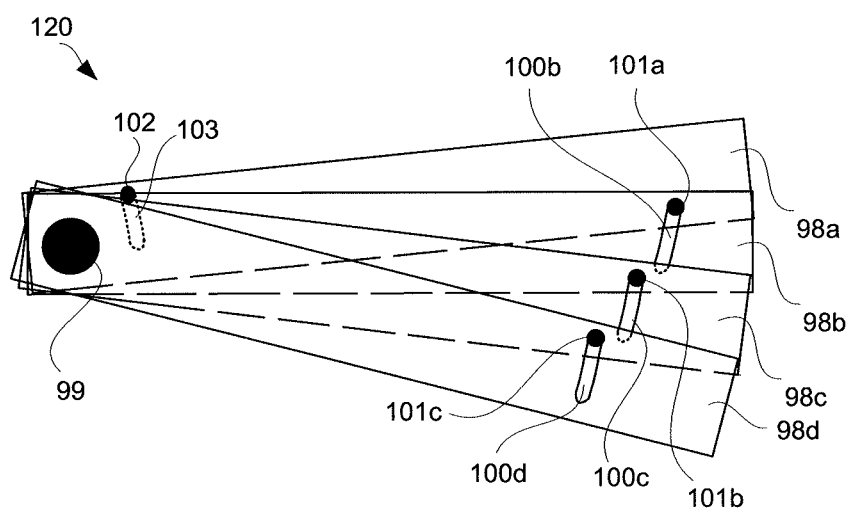
FIG. 11b is a schematic diagram showing a more detailed view of the collapsible protective cover embodiment used in an XRF instrument.

Embodiments of window protector 7 and actuator 71 are shown in FIGS. 3, 8a, 8b, 8c, 11a and 11b. FIG. 3 shows an iris style protector for sealing window 21 that includes actuator 31, cable 35, front detector housing 9, and iris 23 located with detector 2. FIGS. 8a, 8b and 8c show among other things protective cover 61a, gear 65c, support post 65a, spring 65b, securing hole 63, actuator gear 67b, and actuator 67a. FIG. 8a shows cover 61a when in closed (protecting) position 61b. FIGS. 11a and b show a multi-plate protective cover 120 for detector 2 comprised of retractable plates 98a through 98d (i.e. 98a-d) attached to post 99. FIG. 11b shows respective slots 100b-d and initial slot 103, as well as respective pins 101a-c and initial pin 102, all of which are features of the plates depicted in FIG. 11a, but not shown.

Figures 5A, 5B:
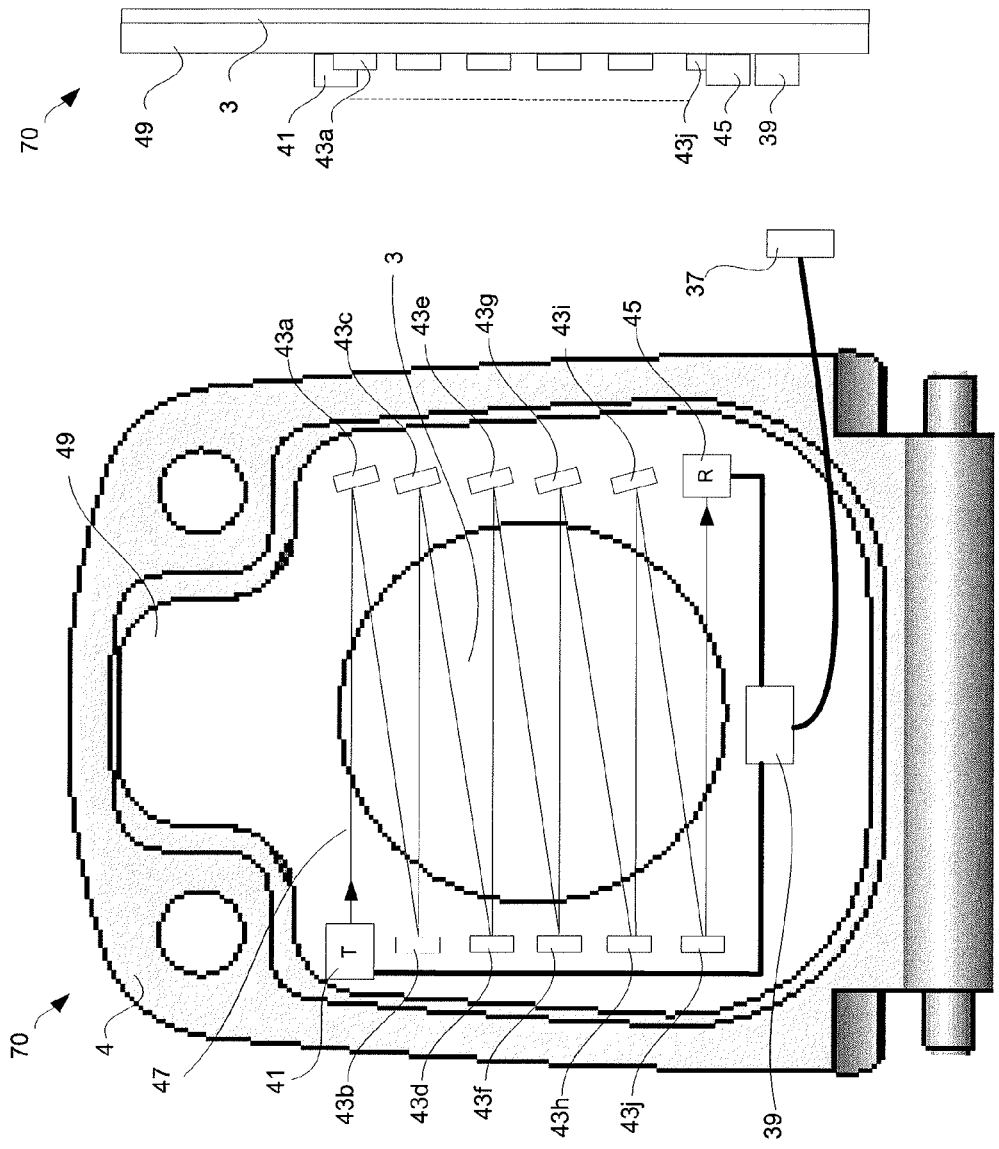
FIGS. 5a and 5b are schematic diagrams showing front and side views, respectively, of an XRF instrument's sealing film mounted on a support frame with an optical presence sensor.

Referring to FIG. 5a, the preferred embodiment of presence sensor 70 is optical presence sensor 49 that is comprised of mirrors 43a through 43j, light source 41, and light beam detector 45, the latter two of which are connected to object presence signal processor 39 by cable 37 as shown in FIG. 6.

Figure 7:
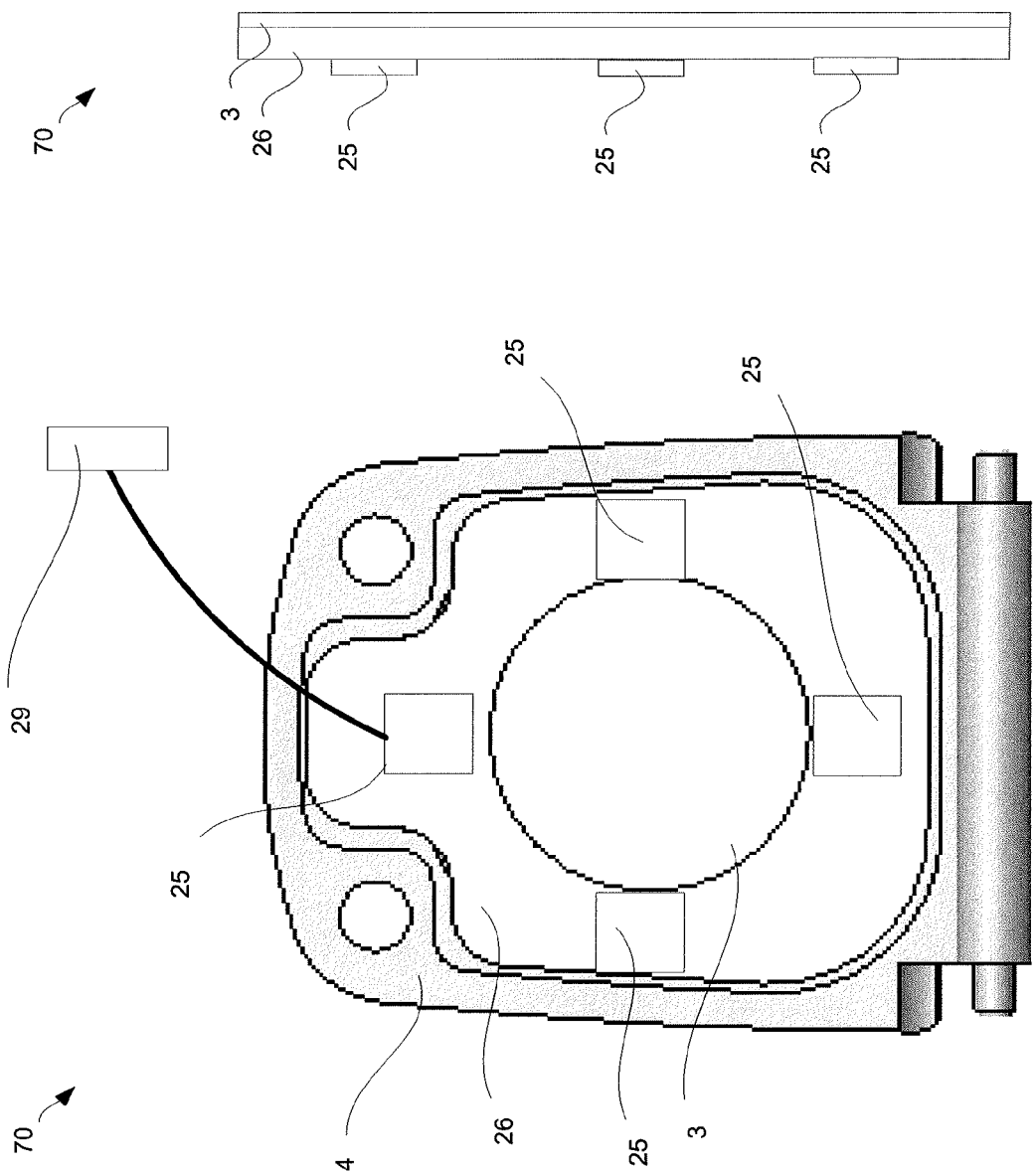
FIGS. 7a and 7b are schematic diagrams showing front and side views of an XRF instrument's sealing film mounted on a support frame with a strain gage or magnetic presence sensor.

FIG. 7 shows alternate embodiments of presence sensor 70 as presence sensor 26 which are optionally at least one strain gage 25 mounted to sealing film 3 that senses stress placed on it by debris 6, or at least one magnetic proximity sensor 25 that senses debris 6 if it is a magnetic material. The signals for sensor(s) 25 are provided through cable 29.

Figure 12:
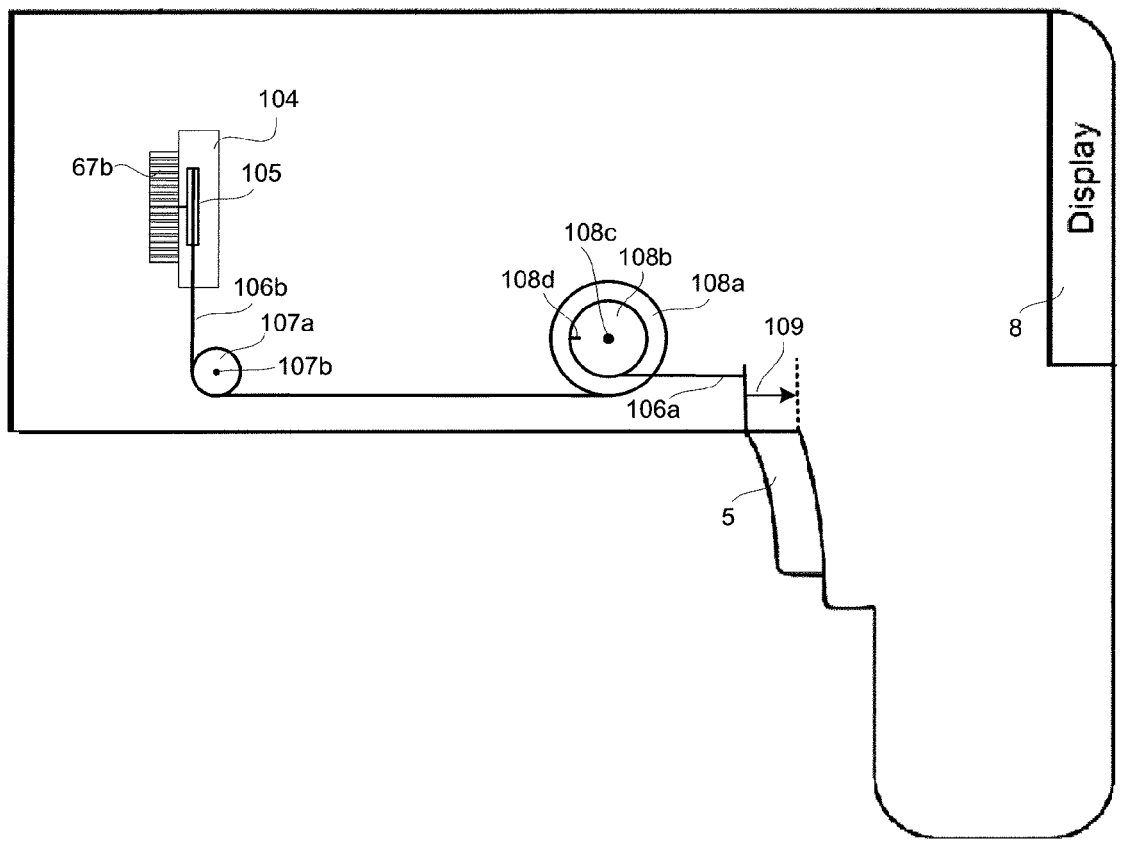
FIG. 12 is a schematic diagram showing a view of the manually operated sealing window protective cover embodiment used in an XRF instrument.

FIG. 12 shows an embodiment of a manual system that translates the stroke distance 109 into the force that drives gear 67b to displace window protector 7 (not shown) when trigger switch 5 is depressed. This mechanical embodiment includes cable 106a attached between trigger switch 5 and point 108d of pulley 108b, and cable 106b attached between pulley 108a and displacement wheel 105 of actuator 104. At least one of trigger switch 5, pulley 108a or b, or wheel 105 is spring loaded to make gear 67b displace window protector 7 to the closed position and return trigger switch 5 to its original position when the user removes the pressure applied by their finger. Pulley 107a may be optionally used to orient cable 106b for cable routing convenience.

Operation & Functions of Embodiments

For all embodiments of the present invention, window protector 7 shown in FIGS. 3, 4, and 8a-c protects sealing window 21 by positioning a cover material between it and debris 6 to prevent contact. Typical operating conditions causing window protector 7 to be in the closed protective position are when: a) the XRF instrument 1 (FIG. 1) is not turned on, b) measurement mode is not active, or c) trigger switch 5 is not depressed. Window protector 7 opens to expose sealing window 21 when trigger switch 5 is depressed and the measurement mode is enabled.

The preferred embodiment of window protector 7 is now described in relation to FIGS. 8a, 8b and 8c. Upon activation of a measurement mode, cover plate 61a of window protector 7 is displaced from position 61b shown in FIG. 8a to expose sealing window 21. Cover plate 61a is fastened to post 65a and gear 65c that is rotated by actuating gear 67b when actuator 67a is engaged. Spring 65b is employed to displace cover plate 61a at a speed faster than achievable by actuator 67a. One end of spring 65b is secured to post 65a and the other end is secured to hole 63 in cover plate 61a. Depending on how it is configured, spring 65b can be employed to provide either rotational tension to cover plate 61a when in the open position as shown in FIG. 8a or closed position 61b. A clutch (not shown) for actuator 67a is disengaged to enable actuating gear 67b to rotate freely, thereby allowing the force exerted by spring 65b to quickly displace cover plate 61a. The use of spring 65b allows the use of a less sophisticated, smaller, lower speed actuator 67a than would be required to displace sealing window 21 at the same speed as the case when spring 65b is used. It should be noted that bi-directional displacement of cover plate 61a by an actuator alone without spring 65b is within the scope of the present disclosure. Furthermore, alternate spring arrangements may be used including, but not limited to, springs that apply pivoting force along their longitudinal direction.

For the applications requiring maximum protection of sealing window 21, spring 65b is configured to apply tension when cover plate 61a is in the open position (i.e. during measurement mode) in order to quickly close when the measurement mode stops. For applications requiring maximum measurement mode speed, spring 65b is configured to apply tension when cover plate 61a is in the closed position (i.e. prior to the start of the measurement mode) in order to quickly open when the measurement mode is activated to start.

FIGS. 11a and 11b depict a fan-like alternate embodiment of cover plate 61a of FIGS. 8a-c that may be used when there are space constraints within XRF instrument 1 (FIG. 4). Indeed, as can be seen in FIG. 11a, the height and width of fan-like cover plate 120 does not go beyond the front area envelope of detector 2, thereby not encroaching on any internal space of instrument except for the direction projecting out of FIG. 11a. The iris embodiment that will be described below in relation to FIG. 3 provides similar advantages in this regard.

Fan-like protective cover plate 120 is comprised of small overlapping plates 98a through 98d (i.e. 98a-d) that expand when post 99 is rotated about its axis in a clockwise direction. Post 99 is rigidly affixed to plate 98d; however, plates 98a-c are free to pivot on post 99 allowing them to be pulled by plate 98d into the closed protective position shown in FIG. 11a. Each plate 98 a-d is held in a fixed circumferential position when maximally displaced to cover the same protection region of sealing window 21 as one piece cover plate 61a of the embodiment shown in FIG. 8a. When in the fully open non-protective position 98a', plates 98a-d are stacked together with their perimeters aligned directly on top of one another.

As shown in FIG. 11b, each plate 98a-c is coupled to its adjacent plate by means of respective pin 101a-c inserted into a respective translation slot 100b-d of the adjacent plate. Accordingly, when plate 98d is maximally displaced it pulls plates 98a-c to move into proper position. It should be noted that the head of each pin 102 and 101a-c is either flush with the top surface of the plate it connects to, or a recess is provided on the bottom of the plate above it to allow unobstructed motion when the plates are moved into position to be stacked in the fully open non-protective position 98a' shown in FIG. 11a. Pin 102 is mounted in a fixed position with respect to the front of sealing window 21 in order to allow stacked plates 99a-d to move completely out of the way of sealing window 21 to the fully open non-protective position 98a'. Furthermore, slot 103 is positioned on plate 98a to allow it to move from non-protecting position 98a' to the protecting position shown in FIG. 11a. It should be noted that the motion control system of fan-like protective cover 120 is the same as described in relation to the embodiment shown in FIGS. 8a-c with reference to actuator 67a, gears 67b and 65c, spring 65b, and post 65a.

Another alternate embodiment of window protector 7 suitable for a constrained space is shown in FIG. 3, wherein sealing window 21 is protected by iris 23 which is coupled to front housing 9 of detector 2 and activated by actuator 31 when a control signal is received by cable 35. Miniature iris devices are well known to those that practice the art of compact camera design.

It should be noted that actuators 67a and 31 of FIGS. 3 and 8b may be driven by: a) an electric motor (not shown) that has its power and control signals provided to it by the XRF instrument's power supply 36 and controller 37 via cable 35, or b) a cable and pulley system as shown in FIG. 12 operable to the depression of trigger switch 5, stroke 109 of which is proportioned to the distance traversed from the fully open and fully closed position of window protector 7. Actuators 67a and 31 are replaced by actuator 104 when the cable and pulley system embodiment is used.

The cable and pulley system of FIG. 12 displaces window protector 7 to a non-protecting open position when trigger key 5 is depressed by stroke distance 109. As the stroke distance is traversed, pulley wheel 108b is pulled about axis 108c by cable 106a that has one of its ends rigidly affixed to notch 108d, thereby causing counterclockwise rotation. Simultaneously, larger radius pulley wheel 108a is rotated in the same direction resulting in an increased stoke distance applied to wheel 105 in actuator 104 which is attached to gear 67b. The increased stroke distance is equivalent to the distance required to move the cover of window protector 7 from a protective closed to a non-protective open position, and is directly proportional to the difference between the circumferences of wheel 108a and 108b. Pulley wheel 107a rotates about axis 107b and is used to change the orientation of cable 106b as may be required by the arrangement of parts within XRF instrument 1. It should be noted that although the foregoing embodiment depicted in FIG. 12 is described in relation to increasing stroke distance 109, it is well within the scope of the present disclosure to reduce or maintain stroke distance 109 by making the radius of wheel 108b greater than or equal to the radius of wheel 108a respectively.

Figure 9:
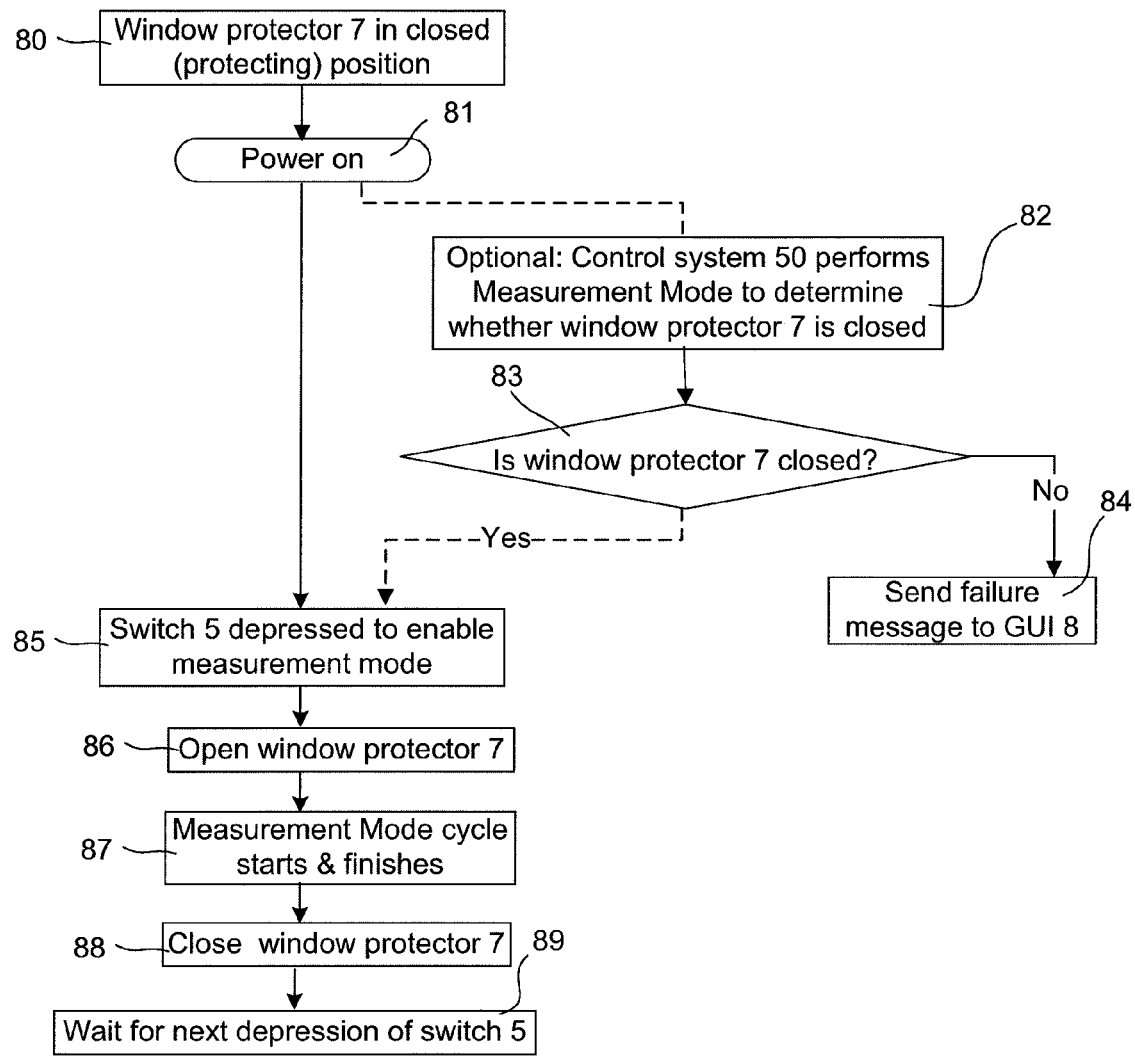
FIG. 9 is a flow chart depicting the primary steps associated with the processing of the controller shown in FIG. 6 for the preferred embodiment of the present disclosure.

A flow chart of the operational steps of the preferred embodiment performed by control system 50 of FIG. 6 is shown in FIG. 9. Before the power is turned on in step 81, window protector 7 is in the closed (protecting) position. After power is turned on in step 81 by a power switch (not shown) and trigger switch 5 is depressed at step 85 to enable a measurement mode controlled by microprocessor system 51, window protector 7 is opened to the non-protective position by window protection controller 37. Immediately afterwards, a measurement mode starts and finishes during step 87, after which window protector 7 returns to the closed (protecting) position at step 88, and then microprocessor system 51 awaits the next depression of trigger switch 5 at step 89.

It should be noted that an optional self-check feature may be invoked via GUI 8, for example, that enables XRF instrument 1 to detect when window protector 7 is in a closed (protecting) position. This is an important feature because when used it lets the user know whether window protector 7 is working properly prior to conducting an inspection session with XRF instrument 1. At step 82, control system 50 performs a measurement mode to determine whether window protector 7 is open or closed. In this case, the measurement mode verifies that the response from detector 2 is what is expected based on the presence of the cover of window protector 7 over detector sealing window 21 (FIG. 2). If it is determined at step 83 that the cover is closed, the process moves on to step 85 to await a depression of trigger switch 5; otherwise, a failure message is sent to GUI 8 at step 84 to notify the user of a malfunction.

Automatic Presence Sensing Embodiments

An additional degree of protection for sealing window 21 can be achieved by providing a means to detect the presence of oncoming obstructions or debris 6 when in measurement mode. The aforementioned presence sensor embodiments 26 and 49 shown in FIG. 6, and FIGS. 5a-b and 7a-b respectively, provide a signal to object presence signal processor 39 which determines when the presence of debris 6 is sensed.

For both options of presence sensor 26 shown in FIGS. 7a and 7b, sensors 35 may be arranged along the perimeter of the opening of support frame 4. The response signal from these presence sensors is connected to object presence signal processor 39 by cable 29 as shown in FIG. 6 in order to monitor the response signal to detect the moment when debris 6 is entering. For the strain gage embodiment, a predetermined degree of strain exerted on sealing film 3 is used as the detection threshold. For the magnetic proximity sensor embodiment, a predetermined degree of magnetic field variation caused by the presence of debris 6 is used as the detection threshold. It is within the scope of the present disclosure to employ two or more of the presence sensor embodiments to implement hybrid embodiments.

FIGS. 5a and 5b show optical presence sensor 49 that provides a trigger signal to object presence signal processor 39 when optical receiver 45 ceases to detect the light beam emanating from light source 41 and traversing path 47. As shown in FIG. 5b, light source 41, mirrors 43a through 43j, and light beam detector 45 are positioned just under the surface of sealing film 3 in order to have path 47 interrupted as soon as practically possible after debris 6 enters.

Figure 10:
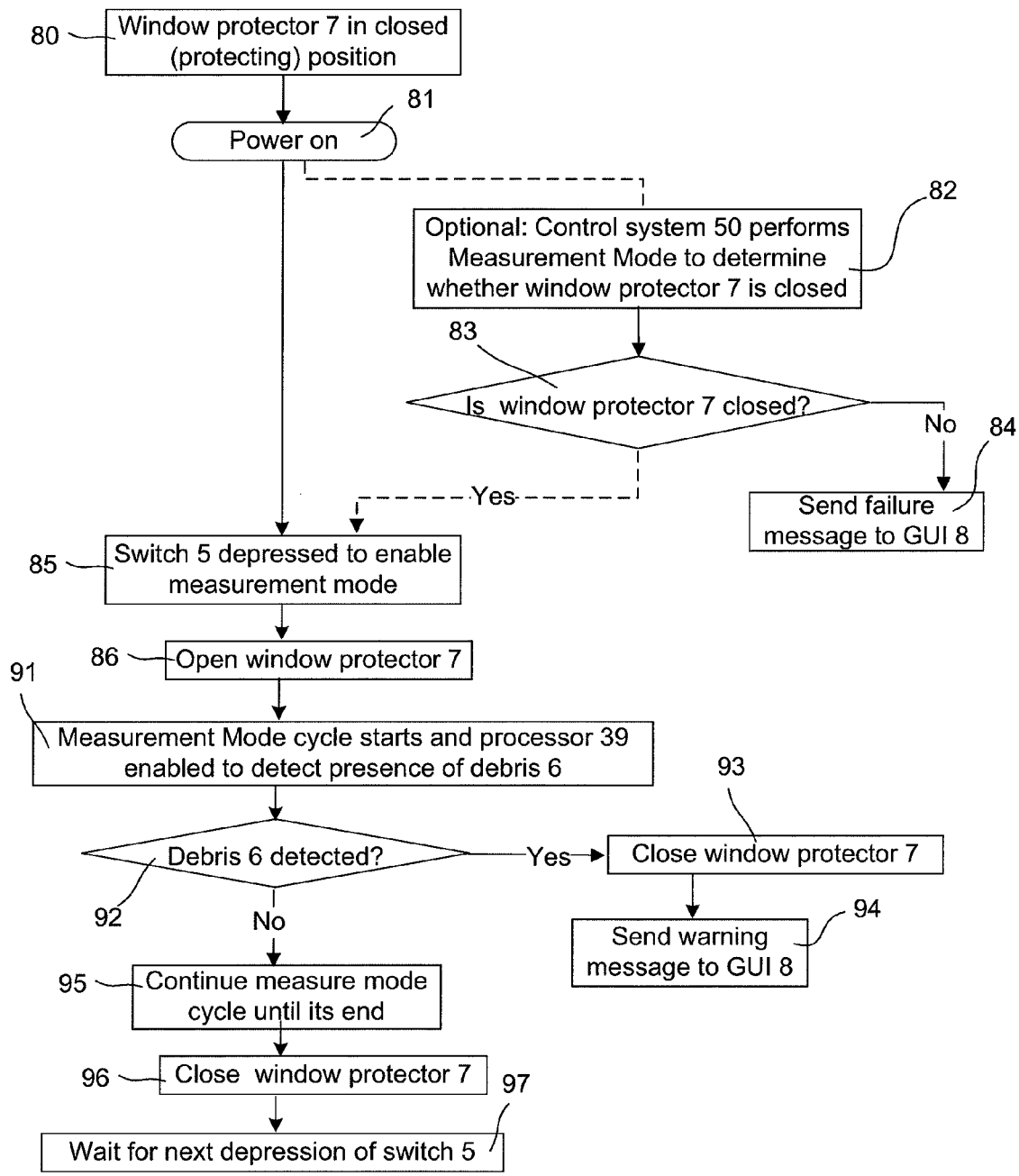
FIG. 10 is a flow chart depicting the primary steps associated with the processing of the controller shown in FIG. 6 for the 'Automatic Presence Sensing Embodiments' of the present disclosure.

A flow chart of the operational steps of the automatic presence sensing embodiments performed by control system 50 of FIG. 6 is shown in FIG. 10. Steps 80, 81, 82, 83, 85 and 86 are the same as described above in relation to FIG. 9, so they need not be described again. After step 86, a measurement mode starts and object presence processor 39 is enabled to detect the presence of debris 6 (FIG. 4) at step 91. If debris 6 is detected, protective cover 7 closes into the protecting position at step 93, thereby preventing damage to sealing window 21 of detector 2. Next, at step 94 a warning message is sent to GUI 8 to let the user know that sealing film 3 has been damaged. If at step 92, debris 6 is not detected the measurement mode continues at step 95. After step 95, window protector 7 returns to the closed (protecting) position at step 96, after which microprocessor system 51 awaits the next depression of trigger switch 5 at step 97.

Exterior Mounted Sealing Window Protector Embodiment

Figure 13B:
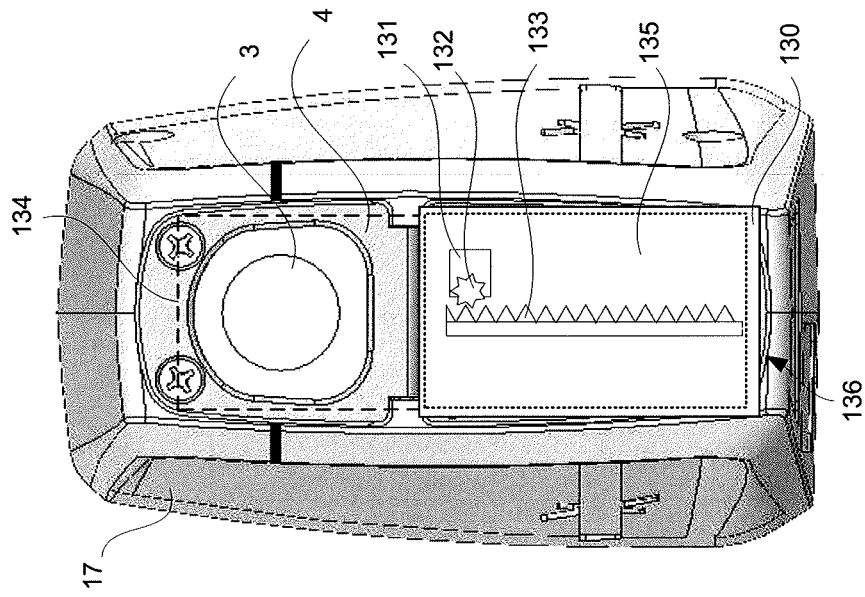
FIGS. 13a and 13b are schematic diagrams showing side and front views of a sealing window protector coupled to the exterior of an XRF instrument in accordance with an embodiment of the invention.
Figure 13A:
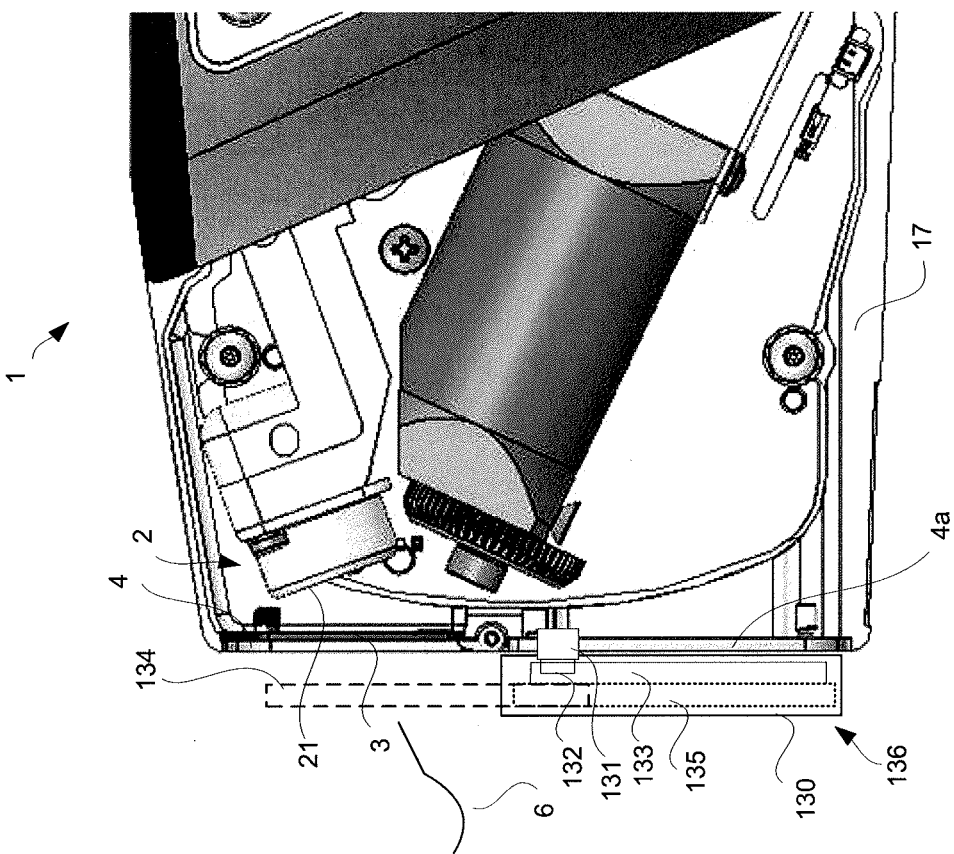

An embodiment of a sealing window protector that is coupled to the exterior front surface of measurement head 17 is shown in FIGS. 13a and 13b. Specifically, protector 136 is positioned on the front face of measurement head 17 with cover 135 operable to be a) moved to position 134 in front of sealing film 3 to protect it from debris 6, and b) moved to expose sealing film 3 and window 21 of detector 2 during measurement mode. The flow chart of FIG. 9 and the narrative associated with it in relation to control system 50 applies to this exterior mounted protector embodiment except that all references to "protector 7" are replaced by "protector 136".

Continuing with FIGS. 13a and 13b, rack and pinion displacement control mechanism used to displace cover 135 into the open and closed 134 position is comprised of actuator 131 with gear 132 engaged with gear rack 133 which is affixed to cover 135. A spring (not shown) may be attached to cover assembly 135 in order to provide the same functions as described above in relation to spring 65b. The movement of cover 135 is constrained to the desired location by means of the side walls of exterior housing 130. Alternatively, a guiding frame may be extended to the perimeter of location 134 if additional positional control and/or mechanism robustness is required. Furthermore, displacement mechanisms other than a rack and pinion type may be used that are known to those skilled in the art.

It should be noted that the exterior mounted protector embodiment may be located within in the interior measurement head 17 as is the case for the embodiments described herein in relation to FIGS. 3, 4, 8a-c, 11a-b, and 12. Furthermore, these interior embodiments may be applied to the exterior of measurement head 17 to provide the same protection provided by the exterior mounted protector 136 embodiment.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

The invention claimed is:

1. An X-ray radiation emitting, material testing device, comprising:
    a hand held device housing including a sealing film mounted on a measurement head of the device;
    a radiation emitter in the device housing and configured to emit test radiation directed at a test object;
    a radiation detector housed inside a detector front housing to detect radiation response of the test object, caused by said test object having been exposed to the radiation of the emitter, wherein the detector front housing is housed within the device housing;
    a sealing window being configured as part of the detector front housing allowing radiation response to reach the detector, and, the detector front housing further comprising, a protective cover mechanism deposited between the sealing film and the sealing window, configured to have at least a closed position covering or obstructing access to said sealing window and an open position exposing said sealing window to allow un-obstructed passage of the radiation response therethrough, and said radiation emitter being located outside said detector front housing.

2. The testing device of claim 1, wherein the protective cover mechanism includes a pivotably mounted cover plate which is pivotable on a pivot located adjacent said sealing window and a moving mechanism which is configured to move the cover plate between said closed position and said open position.

3. The testing device of claim 1, wherein said protective cover mechanism comprises an iris mechanism with plural plates which are movable between a first position which covers said sealing window and a second position which exposes said sealing window to radiation from said test object.

4. The testing device of claim 1, wherein said protective cover mechanism comprises a fan-like cover with a plurality of plates that are configured to be movable from an overlapped, stacked state where the plates overlap one another to expose the sealing window and a spread-apart state in which the plates cooperate to cover said sealing window.

5. The testing device of claim 1, wherein said protective cover mechanism comprises a cover movably mounted on a front surface of said device housing, to move between said open position and said closed position.

6. The testing device of claim 1, further including a debris detector configured to detect the presence of debris located adjacent the sealing window.

7. The testing device of claim 6, wherein the debris detector comprises at least one strain sensor mounted to a sealing film that provides a signal indicative of debris when the debris imparts strain on the sealing film that is sensed by said at least one strain sensor.

8. The testing device of claim 6, wherein the debris detector comprises an optical detector that detects the presence of debris located adjacent the sealing window.

9. The testing device of claim 6, wherein the debris detector comprises a magnetic proximity sensor.

10. The testing device of claim 6, further comprising a user actuated trigger switch, configured, when activated, to cause the protective cover mechanism to move to the open position to allow the measurement mode to occur.

11. The testing device of claim 10, wherein said protective cover mechanism is configured to automatically and immediately return to said closed position upon detection of said debris.

12. The testing device of claim 6, further including a moving mechanism for the protective cover mechanism, said moving mechanism being responsive to said debris detector to cause the protective cover mechanism to automatically move to said closed position.

13. The testing device of claim 12, wherein said moving mechanism includes a biasing element which acts to return the protective cover mechanism to its closed position whenever electrical power is not provided to the testing device.

14. The testing device of claim 12, wherein the moving mechanism is a mechanical mover.

15. The testing device of claim 12, wherein the moving mechanism comprises a cable and pulley system.

16. The testing device of claim 12, wherein said moving mechanism comprises a spring which is structurally located to accelerate movement of the protective cover mechanism to the closed position.

17. The testing device of claim 1, wherein said radiation emitter is an X-ray emitter and wherein said radiation detector is one of a silicon drift detector or PiN diode detector.

18. The testing device of claim 1, wherein said test device comprises a handheld, X-ray fluorescence (XRF) instrument.

19. The testing device of claim 1, wherein said sealing window is made of a thin, fragile material.

20. The testing device of claim 1, further including a process controller, a display, and a graphical user interface (GUI) that is configured to inform a user whenever the protective cover is in the open position.

21. A method for testing an object with X-rays, the method comprising:
providing a radiation emitting, material testing device which includes a hand-held device housing; a radiation emitter in the device housing and configured to emit radiation directed at the test object; a radiation detector housed inside a detector front housing closed by a sealing window and configured to detect radiation of the test object, proximately caused by said object having been exposed the radiation of the emitter; a user actuated trigger switch for the radiation emitter; and a protective cover mechanism affixed to the testing device and configured to have at least a closed position covering or obstructing access to said sealing window and an open position exposing said sealing window to allow the unobstructed passage of radiation therethrough, wherein the detector front housing is housed within the device housing and the sealing window is configured as s art of the detector front housing allowing radiation response to reach the detector, and, the detector front housing further comprising the protective cover mechanism being located between a sealing film and the sealing window and wherein said radiation emitter is located outside said detector front housing; and
actuating said trigger switch to cause the protective cover mechanism to move to the open position.

22. The method of claim 21, further comprising:
moving the testing device toward the test object; and
automatically moving the protective cover mechanism to said closed position upon detecting any debris in a path of the testing device toward the test object.

* * * * *